United States Patent [19]

Pryor

[11] 4,332,378

[45] Jun. 1, 1982

[54] AMBULATORY PATIENT SUPPORT STAND

[76] Inventor: John W. Pryor, 420 N. Cedros, Solana Beach, Calif. 92075

[21] Appl. No.: 140,603

[22] Filed: Apr. 15, 1980

[51] Int. Cl.$^3$ .............................................. A61H 3/04
[52] U.S. Cl. ...................................... 272/70.3; 135/67; 211/205; 248/125; 248/188.7
[58] Field of Search ............... 272/70.3, 70.4, 70, 272/33 R; 128/214 R, 214 E, 214 F, 227, 1 R, 83.5, 673, 674, 25 R; 297/5; 280/1.11 R, 1.186, 87.02 R, 87.02 W, 289 R; 135/67; 248/121, 122, 124, 125, 188.7, 158, 161, 98; 211/205

[56] References Cited

U.S. PATENT DOCUMENTS

| | | | |
|---|---|---|---|
| 320,462 | 6/1885 | Cowing | 272/70.3 |
| 2,355,569 | 8/1944 | Smith | 272/70.3 UX |
| 2,600,547 | 6/1952 | Klein et al. | 248/158 X |
| 2,923,513 | 2/1960 | Johnson | 248/188.7 |
| 3,298,367 | 1/1967 | Bergman | 128/214 R |
| 3,533,583 | 10/1970 | Azim | 248/125 |
| 3,662,980 | 5/1972 | Kantor et al. | 248/188.7 X |
| 3,888,442 | 6/1975 | Comeaux | 248/98 |
| 4,060,214 | 11/1977 | Metcalf | 248/188.7 X |
| 4,086,932 | 5/1978 | Richardson | 272/70.3 X |
| 4,087,106 | 5/1978 | Winchell | 280/87.04 R X |

FOREIGN PATENT DOCUMENTS

| | | | |
|---|---|---|---|
| 432432 | 3/1948 | Italy | 272/70.3 |
| 619106 | 3/1961 | Italy | 248/125 |
| 707256 | 5/1966 | Italy | 211/205 |
| 321317 | 6/1957 | Switzerland | 272/70.4 |
| 278136 | 10/1927 | United Kingdom | 248/161 |

Primary Examiner—Richard J. Apley
Assistant Examiner—Arnold W. Kramer
Attorney, Agent, or Firm—Brown & Martin

[57] ABSTRACT

The stand provides wheeled support for ambulatory patients. Wide span legs, together with the low center of gravity, and a low horizontal push point are utilized. The patient grips the device through a toroidal ring grip. Intravenous bottles may be suspended from a pole supported above the grip. Large rubber casters are provided.

19 Claims, 2 Drawing Figures

AMBULATORY PATIENT SUPPORT STAND

BACKGROUND OF THE INVENTION

The benefits of making hospital patients ambulatory as soon as possible have been documented for some time. The benefits include a shorter post operative recovery and shorter hospital stay. However, due to the limitations of existing equipment it is impracticable for many patients to freely move about. For example, in the case of a patient having a newly-fitted leg-prothesis it may be dangerous for the patient to attempt to move about with existing walkers because of the unnatural gait and resulting unbalance that is produced by lifting and moving the walker frame. Similarly, for patients who must continuously receive intravenous (IV) solutions, there is no current IV stand which can be safely moved along with the patient without danger of upsetting the stand or causing the patient to trip and fall. Present stands have a relatively narrow base, small diameter casters and incorporate a vertical pole with no grip at which the patient may grasp the stand. It has been determined that a patient normally grasps a vertical support at or near chest height. Thus, in moving the stand while attempting to walk, the patient exerts a horizontal force on the stand which has the effect of a long lever arm operating around the relatively narrow base. The possibility of upset is especially great if the castered wheels run into an obstruction or if they are pushed along a carpet. For the same reason, if the patient stumbles slightly and exerts an extra force on the stand, the stand may fall. Even if the stand does not fall the patient will not be able to lean against the tipping stand for the additional support that would permit him to recover. To counteract the upsetting tendency, some patients will attempt to move closer to the vertical support of the stand but in doing so they increase the likelihood that they will trip on a leg of the base. Accordingly, for many otherwise ambulatory patients, there is no safe way for them to move about alone. Under these circumstances they either must be assisted by a nurse or other hospital assistant (with the obvious increase in the hospital costs) or must be confined to bed.

It is therefore desirable to provide an ambulatory patient support stand which has reduced tendency to tip over when pushed by the patient, and which provides support to the patient should the patient trip while walking.

SUMMARY OF THE INVENTION

An exemplary embodiment of the invention overcomes the disadvantages and deficiencies noted with respect to prior art IV stands by providing an ambulatory patient support stand with a horizontal gripping element mounted low on the vertical support of the stand so that the patient reaches down to grasp it. The horizontal arrangement of the grip makes it practical to use the relatively low grip location because it is more natural for a person to exert a horizontal force when their hands are turned horizontal. As a result of the low grip height, the angle of the force exerted by the patient includes a substantial vertical component which tends to keep the stand from tipping. In addition, the stand is constructed to have a low center of gravity and a wide track to further resist the upsetting tendency. Large castered wheels are provided so that the stand rides easily over small obstructions and carpeted surfaces. In addition to one or more IV bottles, the stand may be utilized to support an infusion pump, oxygen bottle and drainage bag for patients requiring these devices. The low center gravity of the stand is enhanced when the grip element is made of a lightweight plastic material which is further desirable because that plastic is non-conductive and this reduces the shock hazard in the event that the conductive portions of the stand should come in contact with wires carrying an electrical current. It has been found desirable to form the horizontal grip element as a toroidal shape surrounding a vertical center support post. In this configuration the grip element performs the additional function of preventing the stand from being moved up to close to vertical objects which might impact an IV bottle knocking it from the support or breaking it.

The invention combines the advantages of a mobile walker for all ambulatory patients with the features of an IV stand. Substantial improvements in the upset characteristics of the stand are obtained by lowered center of gravity or lowered push point. When both of these features are incorporated, an extremely stable stand is produced.

Further advantages of the invention will become more apparent on a reading of the following detailed description together with the drawings in which like reference numerals refer to like parts throughout and in which:

DETAILED DESCRIPTION OF THE DRAWINGS

Figure 1:
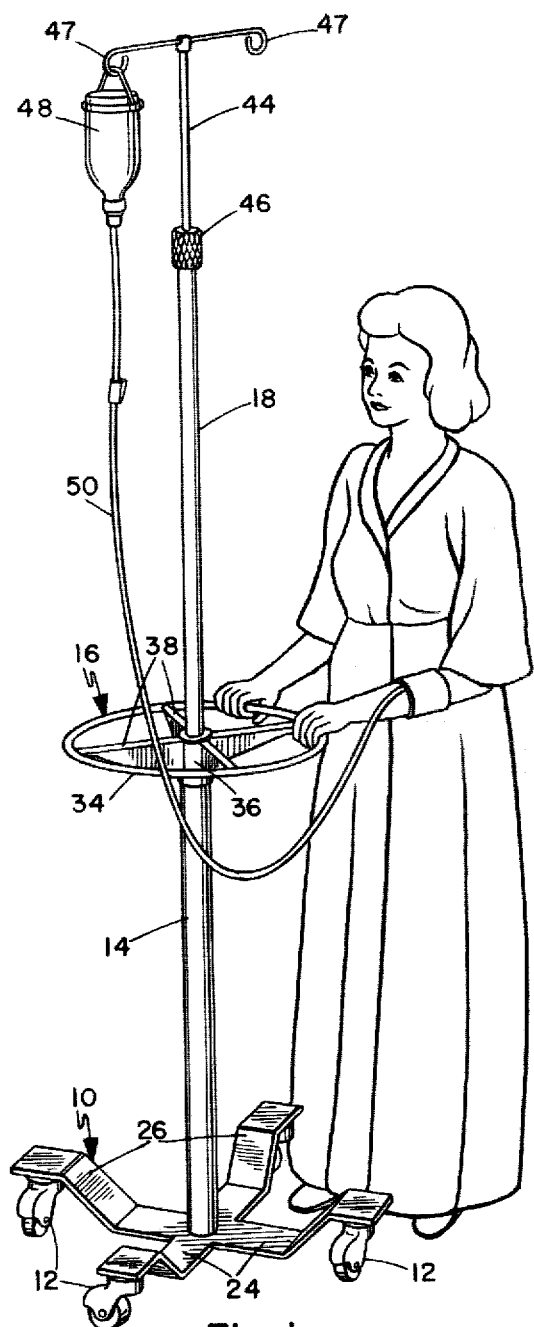
FIG. 1 is a perspective view showing the ambulatory patient support stand in use.

Referring now to the drawings there is illustrated the ambulatory patient support stand. The base 10 is supported from the floor by four castered wheels 12. Vertical support is provided by the central support column 14. The push grip 16 is carried on the support column 14. IV pole 18 is received coaxially within the support column.

Figure 2:
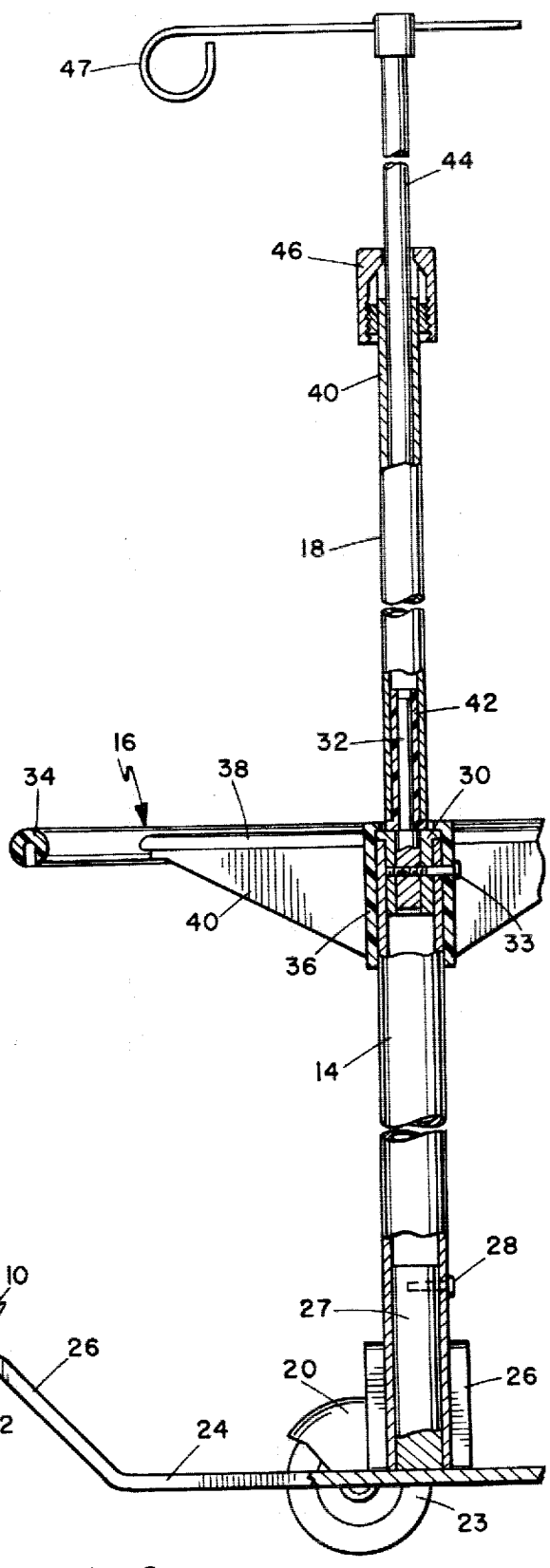
FIG. 2 is an enlarged side elevation view of the stand with portions cut away.

Referring particularly to FIG. 2, the casters 12 are illustrated as incorporating caster mounts 20, mounted on the base 10 by vertical-axis bearings 22. Large caster wheels 23 are received on the horizontal axes 25. It has been found that substantial improvement in the rolling characteristics of the stand are obtained by maintaining a wheel diameter in excess of 6.5 centimeters. The use of casters having an outer diameter of 7.62 centimeters is specifically preferred, as is the use of soft neoprene for the wheel material.

The base 10 is formed of four rectangular arms 24 which have a vertical offset 26 near their outer ends. By virtue of the offset 26 the weight of the center portion of the base is at a lowered relative relationship which augments the stability of the stand. At the axial center of the stand there is mounted a base mating post 27.

The horizontal distance from the center of post 27 to the tip of an arm 24 is at least 10 inches and preferably 12 inches producing a wide stance without unnecessarily limiting access through narrow passageways.

Support column 14 is received over the mating post 27 and held in place by a retention bolt 28. At the upper end of support column 14 a flanged bushing 30 is received. The push grip 16 is received over the bushing 30 and a pole mating post 32 received within bushing 30. The several parts are held in assembled relation by a retention bolt 33.

As will appear most particularly from FIG. 1 the push grip is in the form of a toroidal grip element 34 supported from a central hub 36 by spokes 38 and webs 40. In order to maintain the lowest possible center of gravity the push grip 16 is desirably molded of a lightweight plastic material. Glass-fiber impregnated nylon has been found particularly suitable for the purpose as it combines strength with lightweight. The diameter of the grip element 34 is desirably substantially 1.9 centimeters which is easily grasped by a wide range of individuals without being excessively bulky. The toroidal grip element is spaced from the central axis of the apparatus by a distance in excess of 15 centimeters. It has been found most desirable to locate the push grip at a distance of 21.6 centimeters from the central axis. By locating the push grip spaced from the central axis the device is more easily accepted by patients because the patient does not need to reach as far for the push grip and at the same time the patient's arms fall to a more nearly vertical posture which increases the vertical force transmitted to the device and thereby its stability. The importance of the horizontal spacing of the grip element 34 is particularly significant when the patient stumbles or otherwise loses their balance slightly because the patient is nearly over the point of support and therefore can regain their balance without upsetting the stand.

The height of the push grip has been found to be particularly important in the overall performance of the stand. Given a push grip spaced from the central axis of the device, it has been found that for push grip heights of less than 127 centimeters, there is a marked reduction in the tendency of the stand to tip over when any kind of horizontal resistance is met. A further desirable increase in the safety margin is obtained with a push grip height of 89 centimeters or less.

The IV pole 18 is conventional and incorporates a tube 40 which is received over the post 32 through a telescoped sleeve 42. A pole extension 44 is received within the tube 40 and held in an adjusted position by the knurled pole clamp 46. At the upper end of the pole 44, an IV hanger is mounted, providing mounting hoops 47 for two IV bottles such as the IV bottle 48 illustrated. The necessary pressure to create the proper flow from the IV tube 50 is obtained by vertically adjusting the pole 44 within the tube 40. The overall height range for the IV bottle is comparable to that of conventional IV stands and ranges from 172 centimeters at its lowest point to 252 centimeters at its fullest extension. Not including the weight of any IV bottle or other attachments, the center of gravity of the stand is maintained below 30 centimeters and preferably below 26 centimeters. In relationship to the push grip height, the above dimensions insure that the ratio of push grip height to center of gravity height is less than five to one.

Having described my invention I now claim:

1. An ambulatory patient support stand comprising:
   a wheeled base having a central axis and adapted to move over a supporting surface;
   an elongated vertical support member extending upwardly from said base on said axis;
   a push grip mounted to and radially spaced from said support member, said grip at least partially surrounding and being substantially concentric with said support member, said grip being vertically spaced from said base and being positioned intermediate the ends of said support member at approximately hip height for a person in erect position; and
   additional support means associated with and extending from said support member to removably retain external devices.

2. The ambulatory patient support stand according to claim 1, wherein:
   said grip is toroidal in shape.

3. The ambulatory patient support stand according to claim 1, wherein:
   the diameter of said grip is substantially 1.9 centimeters.

4. The ambulatory patient support stand according to claim 1, wherein:
   the grip is non-electrically conductive.

5. The ambulatory patient support stand according to claim 1, wherein:
   the center of gravity of said stand is no more than 30 centimeters above the floor engaging portion of said wheeled base.

6. The ambulatory patient support stand according to claim 1, wherein:
   said base comprises three or more arms extending horizontally from a central hub and carrying wheels adjacent their outer ends.

7. The ambulatory patient support stand according to claim 6 wherein said base incorporates at least four arms and wheels.

8. The wheeled stand according to claim 7 wherein said wheels have a diameter in excess of 6.5 centimeters.

9. The wheeled stand according to claim 7 wherein said arms are offset adjacent their outer ends vertically above their hub ends.

10. The support stand recited in claim 1 whereby forces normally applied by the erect person to said push grip to move said support stand along its supporting surface include a substantial vertical component, thereby contributing to stability of said support stand.

11. The support stand according to claim 1 wherein the radial distance between said grip and said support member is at least 15 centimeters.

12. The support stand according to claim 1 wherein said push grip comprises a spoked wheel having a hub mounted on said support member and a plurality of spokes extending between said hub and said grip.

13. The ambulatory patient support stand according to claim 12, further including:
   vertical webs extending horizontally from said hub and received on the underside of said spokes.

14. The support stand according to any one of claims 1, 11 or 12 wherein said push grip is spaced vertically above the bottom of said base by less than 127 centimeters.

15. The support stand according to claim 14 wherein the vertical spacing of said push grip is substantially 89 centimeters above the bottom of said base.

16. The support stand recited in claim 15 wherein the center of gravity of said support stand is more than one fifth the vertical spacing of said push grip above the bottom of said base.

17. The support stand according to claim 16 wherein said center of gravity is substantially three tenths of the vertical spacing of said push grip above the bottom of said base.

18. The support stand recited in claim 14 wherein the center of gravity of said support stand is more than one fifth the vertical spacing of said push grip above the bottom of said base.

19. The support stand according to claim 18 wherein said center of gravity is substantially three tenths of the vertical spacing of said push grip above the bottom of said base.

* * * * *